(12) United States Patent
Spicer et al.

(10) Patent No.: US 9,296,666 B2
(45) Date of Patent: Mar. 29, 2016

(54) PYROLYSIS FURNACE TUBE JOINT

(71) Applicant: ExxonMobil Chemical Patents Inc., Baytown, TX (US)

(72) Inventors: David B. Spicer, Houston, TX (US); Christopher C. Penney, League City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 254 days.

(21) Appl. No.: 14/178,486

(22) Filed: Feb. 12, 2014

(65) Prior Publication Data

US 2014/0257001 A1    Sep. 11, 2014

Related U.S. Application Data

(60) Provisional application No. 61/773,186, filed on Mar. 6, 2013.

(30) Foreign Application Priority Data

Apr. 12, 2013  (EP) .................................... 13163458

(51) Int. Cl.
| | |
|---|---|
| *C07C 4/02* | (2006.01) |
| *C07C 4/04* | (2006.01) |
| *B01J 6/00* | (2006.01) |
| *B01J 8/06* | (2006.01) |
| *B01J 19/00* | (2006.01) |
| *B01J 19/24* | (2006.01) |
| *C10G 9/20* | (2006.01) |
| *F16L 13/02* | (2006.01) |
| *B01J 19/02* | (2006.01) |

(Continued)

(52) U.S. Cl.
CPC . *C07C 4/04* (2013.01); *B01J 6/008* (2013.01); *B01J 8/062* (2013.01); *B01J 19/0026* (2013.01); *B01J 19/02* (2013.01); *B01J 19/245* (2013.01); *B01J 19/2425* (2013.01); *C10G 1/00* (2013.01); *C10G 9/20* (2013.01); *C10G 9/203* (2013.01); *C10G 9/36* (2013.01); *C10G 11/00* (2013.01); *C10G 31/06* (2013.01); *F16L 13/02* (2013.01); *B01J 2208/00504* (2013.01); *B01J 2219/00024* (2013.01); *B01J 2219/00157* (2013.01); *B01J 2219/00772* (2013.01); *B01J 2219/0286* (2013.01); *C10G 2300/1081* (2013.01); *C10G 2300/4056* (2013.01); *C10G 2400/20* (2013.01)

(58) Field of Classification Search
CPC .................................... C07C 4/02; C07C 4/04
USPC .................. 585/650, 648, 652, 920, 921, 922
See application file for complete search history.

(56) References Cited

U.S. PATENT DOCUMENTS

| | | |
|---|---|---|
| 4,827,074 A | 5/1989 | Suwa et al. |
| 6,719,953 B2 | 4/2004 | Di Nicolantonio et al. |

(Continued)

OTHER PUBLICATIONS

"Ethylene" Kirk-Othmer Encyclopedia of Chemical Technology, 1980, XP0002712203, vol. 9, pp. 400-408, p. 400 paragraph 7, p. 401 paragraph 3 through paragraph 4, p. 406, paragraph 2; tables 3-5.

*Primary Examiner* — Thuan D Dang

(57) ABSTRACT

The present invention relates to a tube joint for joining first and second tubes located in a fired heater for heating process fluids, e.g., process heaters and heated tubular reactors both with and without catalyst. The tubes are joined in face-to-face contact, e.g., by welding the tube joint of the first tube to the tube joint of the second tube.

11 Claims, 3 Drawing Sheets

(51) Int. Cl.
*C10G 9/36* (2006.01)
*C10G 31/06* (2006.01)
*C10G 1/00* (2006.01)
*C10G 11/00* (2006.01)

(56) References Cited

U.S. PATENT DOCUMENTS

2005/0131263 A1 6/2005 Wolpert et al.
2011/0316271 A1 12/2011 LaLam

PYROLYSIS FURNACE TUBE JOINT

PRIORITY

This application claims priority to U.S. Provisional Application Ser. No. 61/773,186 filed Mar. 6, 2013 and European Patent Application No. 13163458.6 filed Apr. 12, 2013, the disclosure of which is fully incorporated herein by reference.

FIELD

The present invention relates to a tube joint in a fired heater for heating process fluids, e.g., process heaters and heated tubular reactors, both with and without catalyst. More specifically, it relates to a fired heater of the type which comprises at least one radiant section in which process fluid flowing through a multiplicity of tubes some of which are connected by the tube joint, is heated by radiant energy provided by burners.

BACKGROUND

Light olefins such as ethylene, propylene, butenes, butadiene are produced from the pyrolysis of hydrocarbons at high temperatures (700° C. and above) and low pressures (at or slightly above atmospheric). Conventional pyrolysis processes, such as steam cracking, can be utilized to do this. Other co-products include steam cracked naphtha (SCN), steam cracked gas oil (SCGO) and steam cracked tar (SCT).

Steam cracking of hydrocarbons has typically been effected by supplying the hydrocarbon feedstock in vaporized or substantially vaporized form, in admixture with substantial amounts of steam, to suitable coils made up of tubes in a pyrolysis furnace. It is conventional to pass the reaction mixture through a number of parallel coils which pass through a convection section of the pyrolysis furnace wherein hot combustion gases raise the temperature of the reaction mixture. The reaction mixture then passes through a number of specially designed radiant coils made up of tubes in a radiant section enclosure of the pyrolysis furnace wherein a multiplicity of burners supply the heat necessary to bring the reactants to the desired reaction temperature and effect the desired reactions. Undesirable byproduct molecules from the pyrolysis include coke and asphaltenes. The asphaltene molecules are undesirable because they can foul the surfaces in the process as they condense, and are generally low valued. A substantial amount of the coke deposits on surfaces in the pyrolysis reaction system and eventually must be removed by de-coking.

Pyrolysis furnaces used in steam cracking present some of the most severe operating conditions encountered in the chemical process industries. In addition to the high operating temperatures, the tubes experience coking, carburization, oxidation, creep and thermal cycling during operations. Over the years, furnace temperatures have tended to rise to improve feedstock conversion and desirable product yields, placing increasingly severe operating conditions on the pyrolysis tubes.

An important concern in hydrocarbon cracking processes, such as steam cracking, is the formation of coke. When hydrocarbon feedstocks are subjected to the heating conditions prevalent in a steam pyrolysis furnace, coke deposits tend to form on the inner walls of the tubes forming the cracking coils. Such coke deposits interfere with heat flow through the tube walls into the stream of reactants and raise the tube metal temperature.

A variety of heat-resistant alloy steels have been developed for use in pyrolysis furnaces. Although it is well-known that alloy steels containing a relatively high content of chromium and nickel are useful in constructing heat-resistant pyrolysis tubes having relatively long performance lives, premature tube failure continues to be a problem. One cause of such failure is carburization of the tubes brought about by the extremely high temperatures and carburizing atmospheres encountered. Carburization of such tubes, which results from the diffusion of carbon (e.g., from coke) into the alloy steel, causing the formation of additional carbides, brings about the embrittling of the steel. Once the steel has become embrittled, it is more susceptible to creep rupture failure, and/or brittle fracture due to thermal stress. Carburization often occurs at localized spots in the tubes, and of course when this has proceeded to the point of failure or potential failure, even at only one spot, the tubing must be replaced.

The radiant section coils are fabricated by joining two or more tubes typically by welding. Tube failure often occurs at or near the location of welds joining two tubes. This problem is worsened when relatively high temperature is needed to accomplish the pyrolysis, such as when the feed comprises one or more of ethane, propane, gas oil, crude oil, or other heavy oil.

U.S. Pat. No. 6,719,953 discloses an internally finned U-tube coil, a number of which are enclosed in a fired heater radiant section, and utilization of the same in a process for producing olefins form hydrocarbon feedstocks. This patent discloses at column 6 lines 62-67, an intermediate weld at the bottom of the U-tube coils where the weld is shielded from direct radiation by the adjacent coils. The fins are aligned at this connection.

U.S. Pat. No. 4,827,074 discloses a butt-weld for internally-finned steam cracker tubes. The tubes are utilized for steam cracking naphtha. The patent discloses that a conical counterbore of ≤75°, preferably in the range of 8° to 30°, lessens the accumulation of coke during steam cracking. The length of the cylindrical counterbore L/2 is fixed in a specified range, the range depending on the average distance along a diameter between the outside of the tube and the bottom of the tube's fins (grooves) and the average height of the fins. When L is smaller than this range, coke is observed to adhere in the counterbore region. When L is larger than this range, high turbulence leads to hot-spots.

There is still a need for an improved tube joint technology to reduce the frequency of radiant tube failure seen in pyrolysis furnaces, particularly for pyrolysis tubes containing a relatively high content chromium and nickel, such as those utilized at a relatively high pyrolysis temperature.

SUMMARY

Methods and apparatus used in accordance with the present invention are particularly well suited and advantageous for pyrolysis of normally liquid or normally gaseous hydrocarbon feedstocks such as ethane, propane, ethane-propane mixtures (E/P mix), naphtha or gas oil to produce less saturated products, such as acetylene, ethylene, propylene, butadiene, etc. Other suitable feedstocks include one or more of vacuum gas oil, crude oil, resid, or resid admixtures, including those comprising ≥about 0.1 wt. % asphaltenes. Optionally, the pyrolysis furnace has at least one separation device (sometimes referred to as flash pot or flash drum) integrated therewith for upgrading the feedstock. Such vapor/liquid separator devices are particularly suitable when the feedstock component contains ≥about 0.1 wt. % asphaltenes.

The present invention will be described and explained in the context of hydrocarbon pyrolysis, particularly steam cracking to produce ethylene and other unsaturated co-products.

In one embodiment, the invention relates to a joined pyrolysis-furnace tube comprising:

(A) a first pyrolysis-furnace tube, the first pyrolysis furnace tube having (i) an outer surface, (ii) an inner surface, (iii) first and second faces, and (iv) the inner surface having N fins, each fin comprising a fin tip adjacent to two fin roots, wherein (a) the outer surface and the fin roots are separated by an average distance $t_1$, (b) each fin tip protrudes inward an average distance $t_2$ from the fin root, (c) the first pyrolysis furnace tube comprises ≥17 wt. % chromium, and ≥15 wt. % nickel, based on the weight of the first pyrolysis furnace tube, and (d) N≥6;

(B) a second pyrolysis-furnace tube, the second pyrolysis furnace tube having (i) an outer surface, (ii) an inner surface, (iii) first and second faces, and (iv) the inner surface having N' fins, each fin comprising a fin tip adjacent to two fin roots, wherein (a) the outer surface and the fin roots are separated by an average distance $t_1'$, (b) each fin tip protrudes inward an average distance $t_2'$ from the fin root, (c) the second pyrolysis furnace tube comprises ≥17 wt. % chromium, and ≥15 wt. % nickel, based on the weight of the second pyrolysis furnace tube, and (d) N'≥6; and (C) a tube joint, the tube joint connecting the first and second pyrolysis furnace tubes and being open to the flow of fluid, wherein
  (i) the second face of the first pyrolysis furnace tube is joined to the first face of the second pyrolysis-furnace tube, the second face of the first pyrolysis-furnace tube having substantially the same exterior cross-section as the second pyrolysis-furnace tube,
  (ii) the second face of the first pyrolysis tube has (a) a first counterbore extending away from the second face to a first location a distance L/2 into the first furnace tube, the first counterbore being a substantially cylindrical counterbore with L being in the range of from $(t_2/t_1) \cdot 2.5$ cm to $(t_2/t_1) \cdot 12.7$ cm, and (b) a second counterbore, the second counterbore being a conical counterbore beginning at the first location and extending outward at a conical angle in the range of from 5.0° to 20.0°, and
  (iii) the first face of the second pyrolysis tube has (a) a first counterbore, the first counterbore being a substantially cylindrical counterbore extending away from the first face to a second location a distance L'/2 into the second furnace tube, with L' being in the range of from $(t_2'/t_1') \cdot 2.5$ cm to $(t_2'/t_1') \cdot 12.7$ cm, and (b) a second counterbore, the second counterbore being a substantially conical counterbore beginning at the second location with the conical angle being in the range of from 5.0° to 20.0°.

In another embodiment, the invention relates to a hydrocarbon conversion process, comprising:

(1) providing a first mixture comprising water and hydrocarbon, the hydrocarbon comprising ≥75.0 wt. % of alkane having two or three carbon atoms and mixtures thereof;

(2) providing a pyrolysis furnace, the pyrolysis furnace comprising a radiant section comprising one or more radiant coils comprising at least one joined pyrolysis-furnace tube which comprises a first and a second pyrolysis-furnace tube, wherein (a) the first pyrolysis-furnace tube, the first pyrolysis furnace tube having (i) an outer surface, (ii) an inner surface, (iii) first and second faces, and (iv) the inner surface having N fins each fin comprising a fin tip adjacent to two fin roots, wherein (a) the outer surface and the fin roots are separated by an average distance $t_1$, (b) each fin tip protrudes inward an average distance $t_2$ from the fin root, (c) the first pyrolysis furnace tube comprises ≥33.0 wt. % chromium and ≥43.0 wt. % nickel, based on the weight of the first pyrolysis furnace tube, and (d) N≥6;

(b) the second pyrolysis-furnace tube, the second pyrolysis furnace tube having (i) an outer surface, (ii) an inner surface, (iii) first and second faces, and (iv) the inner surface having N' fins each fin comprising a fin tip adjacent to two fin roots, wherein (a) the outer surface and the fin roots are separated by an average distance $t_1'$, (b) each fin tip protrudes inward an average distance $t_2'$ from the fin root, (c) the second pyrolysis furnace tube comprises ≥33.0 wt. % chromium and ≥43.0 wt. % nickel, based on the weight of the second pyrolysis furnace tube, and (d) N'≥6; and (c) a tube joint, the tube joint connecting the first and second pyrolysis furnace tubes and being open to the flow of the first mixture, wherein
  (i) the second face of the first pyrolysis furnace tube is joined to the first face of the second pyrolysis-furnace tube,
  (ii) the second face of the first pyrolysis tube has (a) a first counterbore extending away from the first face to a first location a distance L/2 into the first furnace tube, the first counterbore being a substantially uniform counterbore with L being in the range of from $(t_2/t_1) \cdot 2.5$ cm to $(t_2/t_1) \cdot 12.7$ cm, and (b) a second counterbore, the second counterbore being a conical counterbore beginning at the first location and having a conical angle in the range of from 5.0° to 20.0°, and
  (iii) the first face of the second pyrolysis tube has (a) a first counterbore, the first counterbore being a substantially uniform counterbore extending away from the second face to a second location a distance L'/2 into the second furnace tube, with L' being in the range of from $(t_2'/t_1') \cdot 2.5$ cm to $(t_2'/t_1') \cdot 12.7$ cm, and (b) a second counterbore, the second counterbore being a substantially conical counterbore beginning at the second location with the conical angle being in the range of from 5.0° to 20.0°; and (3) conducting the first mixture through the at least one joined pyrolysis-furnace tube to expose the first mixture to a temperature ≥400° C. under pyrolysis conditions and convert at least a portion of the first mixture's alkane to $C_2$ unsaturates.

DETAILED DESCRIPTION

Conventional steam cracking utilizes a pyrolysis furnace which has two main sections: a convection section and a radiant section. The hydrocarbon feedstock typically enters the convection section of the furnace where it is heated and vaporized by indirect contact with hot flue gas from the radiant section and by direct contact with the first mixture's steam component. Typically the steam is supplied at a rate of 0.20 to 1.0 weight steam/weight of hydrocarbon, or preferably 0.20 to 0.50 weight steam/weight of hydrocarbon. The steam-vaporized hydrocarbon mixture is then introduced into the radiant section where the bulk of the cracking takes place. The pyrolysis effluent is conducted away from the pyrolysis furnace, comprising products resulting from the pyrolysis of the feedstock and any unreacted components. At least one separation stage is generally located downstream of the pyrolysis furnace, the separation stage being utilized for separating one or more of light olefin, steam cracked naphtha (SCN), steam cracker gas oil (SCGO), steam cracker tar (SCT), water, unreacted hydrocarbon components. The separation stage can comprise, e.g., a primary fractionator. Generally, a cooling stage, typically either direct quench or indirect heat exchange is located between the pyrolysis furnace and the separation stage.

As indicated in the summary, a variety of hydrocarbon feedstocks are utilized. Particularly attractive yields of $C_2$ unsaturates (ethylene and acetylene) are obtained from feedstocks comprising ethane, propane, and mixtures thereof (e.g., ethane-propane mixtures or "E/P" mix). For ethane cracking, a concentration of at least 75% by weight of ethane is preferred. For E/P mix, a concentration of at least 75% by weight of ethane plus propane is preferred, the amount of ethane in the E/P mix being ≥20.0 wt. % based on the weight of the E/P mix, e.g., in the range of about 25.0 wt. % to about 75.0 wt. %. The amount of propane in the E/P mix can be, e.g., ≥20.0 wt. %, based on the weight of the E/P mix, such as in the range of about 25.0 wt. % to about 75.0 wt. %.

Figure 1:
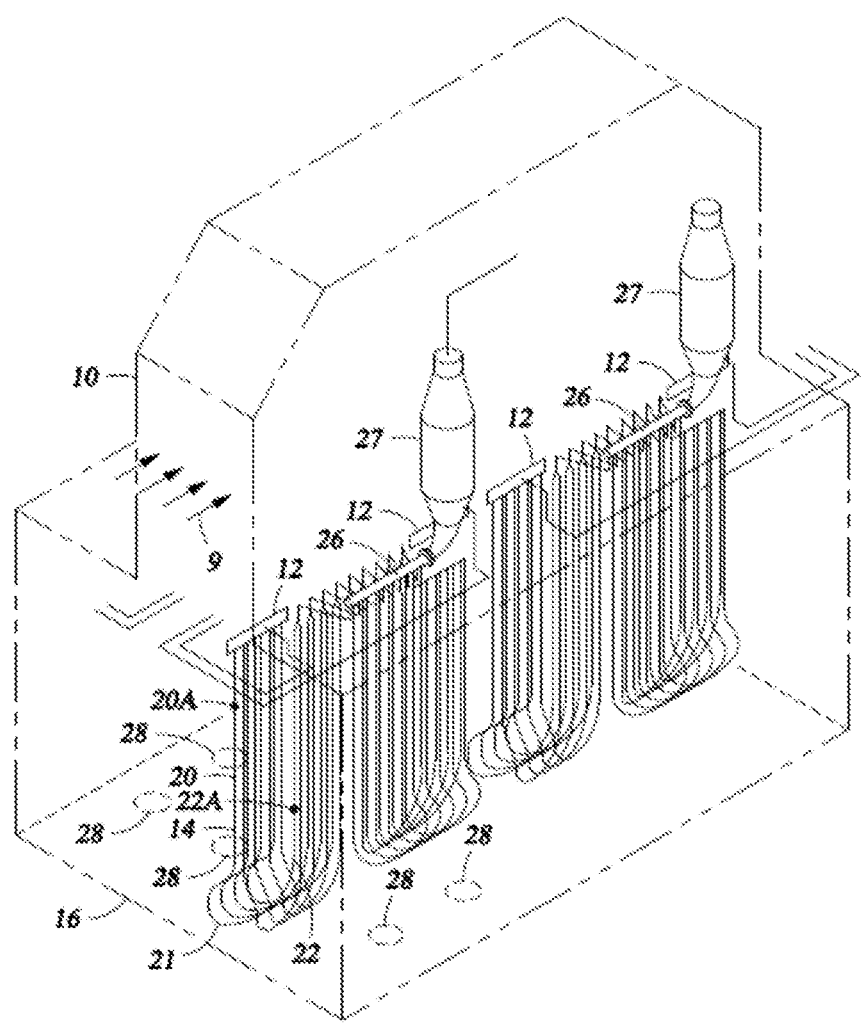
FIG. 1 is a three-dimensional drawing of a pyrolysis furnace showing a typical arrangement of internals.

A representative pyrolysis furnace is illustrated in FIG. 1. Referring to FIG. 1, the feed enters the convection section 10, through one or more inlet lines 9 where it is combined with steam and preheated, e.g., to a temperature in the range of from about 750° F. to about 1400° F. (400° C. to 760° C.) by hot combustion gases. The combustion gases are preferably at a temperature in the range of from about 1500° F. to about 2400° F. (816° C. to 1316° C.). The heated feed-steam mixture (the "process fluid") is then conducted to radiant section inlet distributor 12. From the radiant section inlet distributor 12 the preheated feed enters the radiant coils 14 which are situated inside the radiant section enclosure 16, also known in the art as the radiant box. The radiant section enclosure 16 is typically lined with heat insulating refractory material to conserve heat energy.

The radiant section enclosure includes a plurality of tubes. The end of the tubes which are connected to one or more inlet distributors 12 which introduce the process fluid into inlet legs 20 of the radiant tubes. The opposite end of each of the radiant tubes is an outlet leg 22, which is connected to an outlet header 26 for collecting the radiant section's effluent, which comprises pyrolysis products and any unreacted process fluid. The temperature of the radiant section's effluent is typically in the range of from about 1300° F. to about 2000° F. (700° C. to 1100° C.) leaving the outlet leg of the radiant tube. From there the process fluid is passed to quench exchanger 27 which cool the process fluid to stop the thermal cracking reactions. In another embodiment, not depicted in FIG. 1, the outlet leg of each radiant tube is directly connected to an individual quench exchanger to cool the process fluid. The outlet from each individual quench exchanger is then connected to an outlet header. Such an arrangement is known in the art as a close coupled transfer line exchanger. In yet another embodiment not depicted in FIG. 1, the outlet leg of each tube is connected to a quench point whereby the process fluid is directly contacted with a quench liquid which vaporizes to cool the process fluid.

The residence time in the radiant coil is generally in the range of 0.10 to 2.0 sec, and the pressure is generally in the range of 1.0 to 5.0 bar absolute.

The pyrolysis furnace illustrated in FIG. 1 employs U-tube coils, so called because each coil is shaped somewhat like the letter "U" when viewed in two dimensions. A defining characteristic is that the U-tube coil effectively makes 2 passes through the radiant section enclosure. The U-tube coils are comprised of an inlet leg 20, an outlet leg 22, and a curved or bent portion 21 connecting the inlet leg 20 and the outlet leg 22.

Other embodiments employ a number of passes that is greater or less than 2 passes through the radiant section enclosure. For example a double "U" coil (also commonly referred to as a "W" coil) would have 4 passes. Embodiments utilizing a greater number of passes such as 6, 8, 10, or 12 or more passes could employ, e.g., a serpentine coil. There are a variety of ways known in the art of arranging a plurality of tubes in a radiant enclosure, but the invention is not limited thereto. For example, in certain embodiments, the coils can comprise one or more branched portions. In other embodiments, the outlet leg can comprise one or more branched portions. In yet other embodiments, the inlet leg 20 can comprise more than one branched tube.

The radiant section enclosure contains a plurality of burners 28 for exposing the external surface of the tubes to radiant heat. Conventional burners can be used, including raw gas or pre-mixed burners, but the invention is not limited thereto. In certain embodiments, a variety of flue gas recirculation techniques are utilized to reduce NOx formation in the furnace's combustion effluent. The combustion air source can be, e.g., from one or more of ambient air, preheated air, or gas turbine exhaust.

The invention is not limited to a particular steam cracker configuration. Those skilled in the art will consider the spatial arrangement, location of the burners location of the inlet header and outlet means, and thermal stresses on the tubes themselves in choosing the arrangement of these components. In certain embodiments, each of the tubes lies in a single plane. In other arrangements, the tubes are bent out of plane, primarily to reduce thermal stresses.

The radiant section coils are fabricated by joining two or more tubes typically by welding. Typically the lengths of the individual tubes that are joined are from about 2 feet (61 cm) to about 20 feet (610 cm). The tubes being joined can be the same or different lengths. Typically the tubes are joined in pairs, with the end or face of the first tube butt-welded to the end or face of the second tube. In order to properly create this weld, a weld prep is cut into the end or face of each tube to be joined.

For example, the total length of a U-tube coil is preferably in the range of about 60 ft to about 90 ft (20 m to 27 m). Since it is difficult to manufacture the internally finned tubes in these lengths, two tubes or more might need to be joined with intermediate welds. Referring to FIG. 1, inlet leg 20 can comprise, e.g., two tubes joined at location 20A, and outlet leg 22 can comprise, e.g., two tubes joined at location 22A.

The term tube means an elongated hollow member suitable for fluid transport. Aspects of the invention are also applicable to connectors and/or fittings, such as unions, elbows, "T"s, "Y"s, and to ancillary equipment, e.g., valve means.

Figure 2:
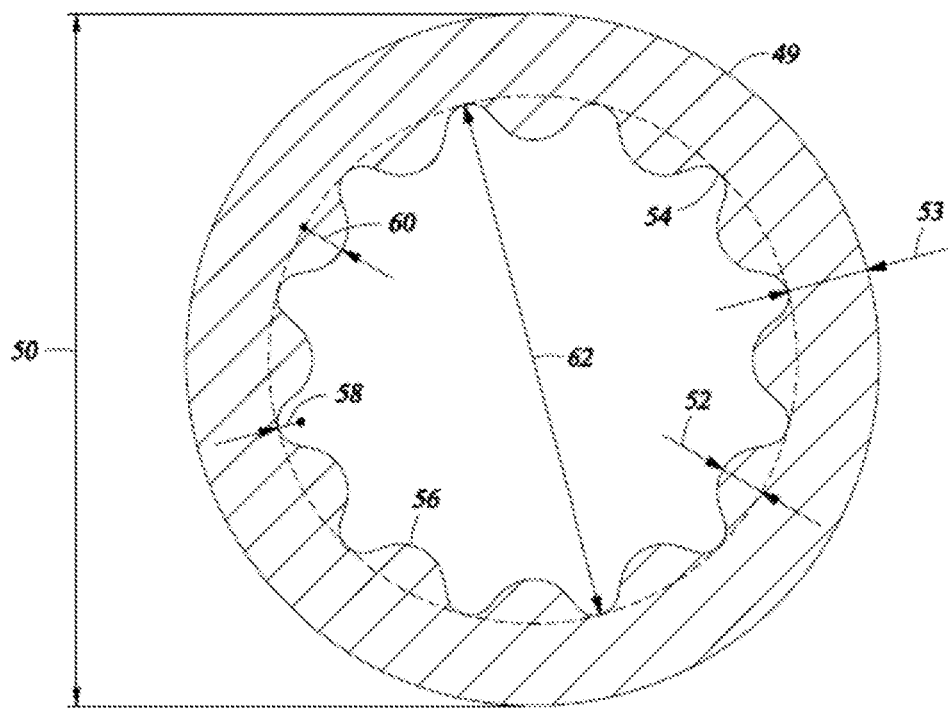
FIG. 2 schematically illustrates a cross-section of a typical internally finned radiant section tube for a pyrolysis furnace.

The tubes can be internally finned to improve heat transfer and decoking efficiency. A cross-section of an internally finned tube is provided in FIG. 2, with the finned tube having an outer surface 49. As shown in FIG. 2, there are 12 fins resembling the shape of a wave when viewed in cross-section on the inner surface of the tube. Each fin has a fin tip 56 adjacent to two fin roots 54. Typically, the tubes have between 6 to 36 fins. In certain embodiments, the fins are oriented substantially parallel to the long axis of the tube. In other embodiments, the orientation of the fins rotates spirally in the longitudinal direction, like the rifling in a gun barrel. Such fins can be described as elongated helixes. Although "wave-shaped" figuring can be utilized for the tube's fins (also commonly referred to as "lands"), the invention is not limited thereto. For example, in certain embodiments, the fins have a triangular or rectangular shape.

The tube's outside diameter 50, designated $D_o$, is in the range of 1.75 inch to 12 inch (4.4 cm to 30.5 cm), preferably 2.0 to 6.0 inch (5 cm to 15.2 cm). The metal thickness at the fin root 53, designated $t_1$, is the minimum metal thickness between the tube's inside and outside surfaces. Typically $t_1$ is in the range of from 0.25 inch to 1.00 inch (0.64 cm to 2.54 cm), or in the range of from 0.25 inch to 0.50 inch (0.64 cm to 1.27 cm). The fin height 52, designated $t_2$, is the distance the fin tip protrudes inward (toward the tube's center), and is equal to the distance between the bottom of the fin root 54 and the top of the fin tip 56. Values for $t_2$ can be, e.g., in the range of from about 0.05 inch to about 0.4 inch (0.13 cm to 1.0 cm), preferably from 0.1 inch to 0.25 inch (0.25 cm to 0.64 cm), typically $t_2 \leq t_1/2$. The number of fins around the circumference of the inside surface of the tubes is not critical, and can be e.g., $\geq 6$, such as in the range of from about 6 to about 36. In certain embodiments, e.g., those using curved fins, the radius of fin root 58 and fin tip 60 can be, e.g., in the range of from about 0.05 inch to about 0.45 inch (0.13 cm to 1.2 cm), preferably 0.1 inch to 0.2 inch (0.25 cm to 0.5 cm). In one embodiment, the fin root radius and fin tip radius are substantially equal. The tube's inside diameter 62, designated $D_i$, is defined as the distance through the center of the tube from fin root to fin root. In certain embodiments, $D_i$ is in the range of from about 1.25 inch to about 10.0 inch (3.175 cm to 25.4 cm), preferably from about 1.5 inch to about 6.0 inch (3.8 cm to 15.2 cm). In certain embodiments, the ratio of the fin height to inside diameter $t_2/D_i$ is in the range of from 0.05 to 0.20, more preferably in the range of from 0.07 to 0.14. A $t_2/D_i$ ratio in this range can provide, e.g., improved heat transfer without excessive pressure drop or undue tendency to plugging.

Stainless steel tubes, e.g., austenitic stainless steel tubes, are suitable for the practice of the present invention. Such tubes are typically fabricated by casting methods and can contain ≥17 wt. % chromium, such as about 17 wt. % to about 40 wt. % chromium, and ≥15 wt. % nickel, such as about 15 wt. % to about 50 wt. % nickel based on the total weight of the alloy.

Such steels include carbon and lower amounts of a number of micro alloying elements such as silicon, molybdenum, manganese, niobium, cobalt, tungsten, tantalum, and aluminum. The balance of the steel after the chromium, nickel, carbon and micro alloy elements is iron. In referring to the iron content of the alloys as constituting the "balance", it is to be understood that impurities as well as other elements and substances may be present. Such other elements and substances may each be present at levels up to about 5 wt. %. Non-limiting examples of such elements and substances include nitrogen, copper, hafnium, rare earth elements, etc. Minor amounts or impurities typically found in such alloys may also be present, as well as tramp elements such as lead, tin, zinc, selenium, etc.

In an embodiment (I), the tube material is an austenitic stainless steel containing about 17 wt. % to about 40 wt. % chromium; about 15 wt. % to about 50 wt. % nickel; about 0.06 wt. % to about 0.6 wt. % carbon; ≤about 2 wt. % manganese; about 1 wt. % to about 2.5 wt. % silicon; ≤about 2 wt. % niobium, ≤about 2 wt. % molybdenum, ≤about 3 wt. % tungsten, ≤about 17 wt. % cobalt, with the balance being iron, wherein all weight percents are based on the total weight of the alloy.

In another embodiment (II), the tube material is an austenitic stainless steel containing about 17 wt. % to about 40 wt. % chromium, about 15 wt. % to about 50 wt. % nickel, about 0.06 wt. % to about 0.6 wt. % carbon, about 1 wt. % to about 2.5 wt. % silicon, ≤about 2 wt. % manganese, ≤about 3 wt. % tungsten, ≤about 2 wt. % molybdenum, ≤about 2 wt. % niobium, with the balance being iron.

In yet another embodiment (III), HK and HP type austenitic stainless steels are used. For example, the HK type steels are generally those containing about 20 wt. % to about 30 wt. % chromium, about 16 wt. % to about 24 wt. % nickel, about 0.2 wt. % to about 0.5 wt. % carbon, about 0.6 wt. % to about 2 wt. % silicon and ≤about 2 wt. % manganese, with the balance being iron. The HP type alloy steels are generally those containing about 20 wt. % to about 30 wt. % chromium, about 30 wt. % to about 40 wt. % nickel, about 0.06 wt. % to about 0.8 wt. % carbon, about 0.6 wt. % to 2 wt. % silicon, about 0.5 wt. % to about 2 wt. % manganese, ≤up to about 2 wt. % molybdenum, ≤about 3 wt. % tungsten, and the balance being iron.

For example, the steel can contain about 25 wt. % chromium and about 35 wt. % nickel plus micro alloying elements. In yet another embodiment, the steel contains about 35 wt. % chromium and about 45 wt. % nickel plus micro alloying elements.

It is understood by those skilled in the art that when referring to nickel and chromium content of an alloy, that normal commercial variation in the concentration of these elements is ±about 2.0 wt. % or ±about 3.0 wt. %. For example, in certain embodiments, the steel contains (i) about 22 wt. % to about 28 wt. % chromium and about 32 wt. % to about 38 wt. % nickel (plus micro alloying elements) or (ii) about 32 wt. % to 38 wt. % chromium and 42 wt. % to 48 wt. % nickel (plus micro alloying elements). All chromium and nickel contents provided in this specification and appended claims represents a nominal value, subject to the normal commercial variations indicated above. It is further understood that all weight percents herein are based on the total weight of the alloy.

The high chromium and nickel content are needed to improve strength and lessen the effect of grain creep at the high temperatures encountered during steam cracking. Unfortunately, the high chromium and nickel content leads to a decrease in tube ductility, resulting in an increased tendency to fracture in the vicinity of the weld joining two tubes.

In embodiments where finned tubes are utilized, it is not necessary to precisely line up the fins in the two sections tubes that are being joined. However, imprecision in fin alignment can result in increased coking at the tube joint, leading to an increase in the tube metal temperature at the joint. This can further increase the tendency to facture in the vicinity of the weld joining the tubes. The effects of misalignment can be lessened or avoided by grinding away the fins in a direction parallel to the tube's long axis for a certain distance from the tube joint. This can be accomplished, e.g., by utilizing a cylindrical counterbore to entirely remove the fins for a certain distance followed by a conical counterbore to ramp the fins to their normal thickness, the counterbore being in the range, e.g., of from about 5° to about 20°.

Figure 3:
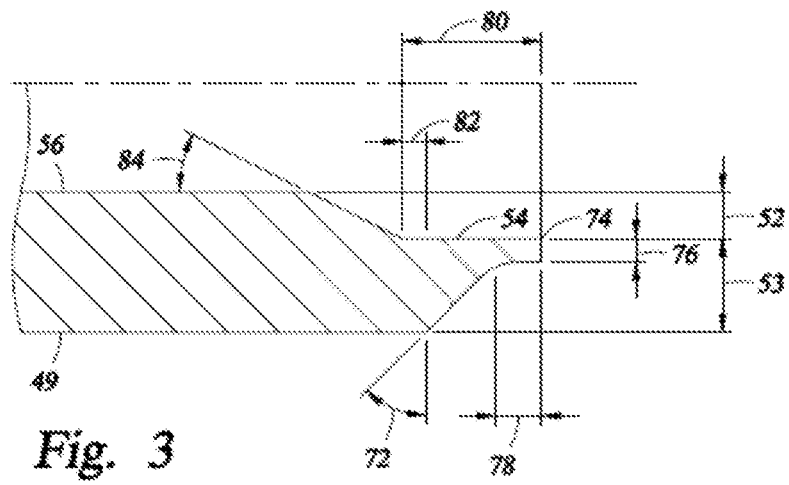
FIG. 3 schematically illustrates a cross-section of a weld prep for joining two internally-finned radiant section tubes.

This approach is illustrated in FIG. 3 which depicts a J-type weld prep for joining two internally finned tubes according to the invention. FIG. 3 shows the weld prep for the internal and external tube surfaces, illustrated from the top of "land" 56 (the point of minimum inside diameter of the tube) to the external (outside) tube surface 49. Dimension 80 represents one half of the total cylindrical counterbore length for the two tubes to be joined. The conical counterbore angle 84 is designated as φ. The J-type weld prep cut into the outer surface of the tube includes a tip 74 of length 78 designated p and thickness 76 designated $t_p$ cut at a weld prep bevel angle 72 designated θ, e.g., about 20°+/−15°, such as 15° to 25°.

Figure 4A:
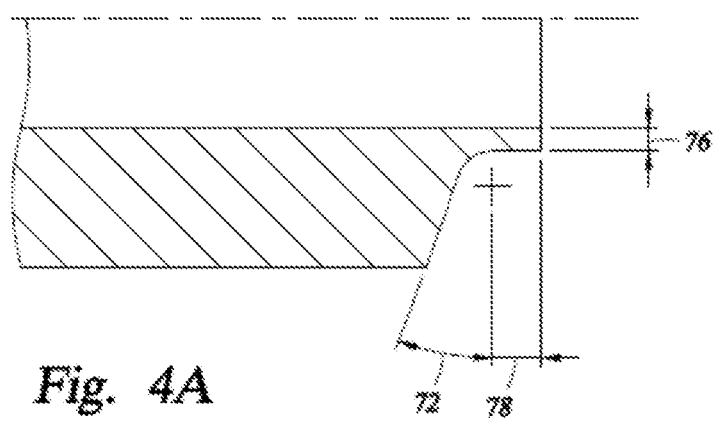
FIG. 4 schematically illustrates J-Bevel (4A) and V-Bevel (4B) weld preps.
Figure 4B:
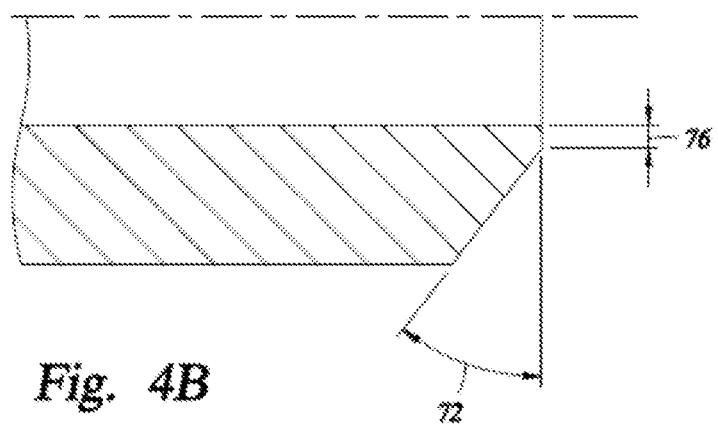

Alternative weld preps for joining the external surfaces of the tubes are shown in FIGS. 4A (illustrating an alternative J weld prep) and 4B (illustrating a V weld Prep). FIGS. 4A and 4B show weld preps for the external surface of the tube, illustrated from the bottom of groove 54 (the point of maximum inside diameter of the tube) to the external tube surface 49. Since FIGS. 4A and 4B illustrate weld preps for joining the external surfaces of adjoining tubes, the internal cylindrical and conical counterbores are not shown. FIG. 4A shows a J weld prep having a steeper angle than the J weld prep of FIG. 3. FIG. 4B shows a V-type weld prep, which can be used for joining the external surfaces of adjacent tubes instead of the J weld preps illustrated in FIGS. 3 and 4A. In this case there is no tip 74, so that the length of the tip 78 is substantially equal to zero, that is p=0. The weld prep bevel angle 72 for the V-type weld prep would be larger than the weld prep bevel angle for the J-type weld prep, e.g., about 38°+/−15°.

The tendency to fracture at the tube joint is overcome by carefully selecting the dimensions of the cylindrical and conical counterbores for fin removal from the inside surface of the tubes to be joined and its relation to the weld prep on the outside surface of the tubes, in order to (i) lessen the effects of stress concentration that might otherwise lead to joint failure when the tube's temperature is cycled from operating temperature to a lower temperature for, e.g., decoking, and (ii) lessen the effects of strain across the weld during operation. In other words, instead of reducing fractures by metallurgically improving ductility (by decreasing the amount of chromium and nickel), which would undesirably lessen the tube's strength and creep resistance, the invention mitigates fracturing by a special mechanical design of the tube joint, as specified in more detail in the following paragraphs.

Firstly, utilizing a relatively shallow conical counterbore angle φ in the range of 5° to 20°, much smaller than the conventional counterbore of up to 75°.

Secondly, it is beneficial to have a minimum counterbore length that is considerably longer than the prior art, e.g., $(t_2/t_1) \cdot 1.0$ inch [25 mm]≤L≤$(t_2/t_1) \cdot 5.0$ inch [127 mm], more preferably $(t_2/t_1) \cdot 1.0$[25 mm]≤L≤$(t_2/t_1) \cdot 2.0$[51 mm]. When L is larger than this range, heat exchange is lessened and the furnace operates less efficiently. When L is smaller than this range, the specified weld prep weakens the butt-weld, especially in the case of steel with high chromium and nickel content as a result of decreased tube ductility.

Thirdly, the relation between the counterbore dimensions and the weld prep is selected to provide an offset C, the thickness of the tube metal being maintained at substantially equal value to $t_1$ over the length of the offset. In FIG. 3, the offset is shown as reference 82. In certain embodiments, C is ≥$t_1/4$, preferably ≥$t_1/2$.

Those skilled in the art will appreciate that the value of C can depend on tube composition and geometry. It has been found that for the specified alloys (I), (II), and (III), the offset C can be calculated from the other tube dimensions by the following formula (I):

$$C = \frac{L}{2} - (p + (t_1 - t_p)\tan\theta) \quad (1)$$

where
θ=weld prep bevel angle
p=tip length for J-type weld prep
p=0 for V type weld prep
$t_p$=tip thickness Certain aspects of the invention will now be described in terms of joining the two adjacent furnace tubes. The invention is not limited to these aspects, and this description is not meant to foreclose other embodiments within the broader scope of the invention.

I. Adjacent Pyrolysis Furncace Tubes Joined Face-to-Face

In certain aspects, the invention relates to joined pyrolysis-furnace tubes comprising the first and second pyrolysis-furnace tubes, and a tube joint joining the first and second tubes.

The first pyrolysis-furnace tube has inner and outer surfaces, and first and second faces. The inner surface has N fins, with each fin comprising a fin tip adjacent to two fin roots, wherein (a) the outer surface and the fin roots are separated by an average distance $t_1$, (b) each fin tip protrudes inward an average distance $t_2$ from the fin root, (c) the first pyrolysis furnace tube comprises ≥17 wt. % chromium, and ≥15 wt % nickel, based on the weight of the first pyrolysis furnace tube, and (d) N≥6.

The second pyrolysis-furnace tube also has inner and outer surfaces, and first and second faces. The inner surface has N' fins, with each fin comprising a fin tip adjacent to two fin roots, wherein (a) the outer surface and the fin roots are separated by an average distance $t_r$, (b) each fin tip protrudes inward an average distance $t_2'$ from the fin root, (c) the second pyrolysis furnace tube comprises ≥17 wt. % chromium, and ≥15 wt. % nickel, based on the weight of the second pyrolysis furnace tube and (d) N'≥6. The first and second pyrolysis furnace tubes are connected at the tube joint. The tube joint is configured into the second face of the first tube and the first face of the second tube so that the first and second tubes can be joined, e.g., by welding. The tubes (including the tube joint) are open to the flow of fluid. For example, the tubes and tube joint are open to the flow of fluid into the first face of the first tube, through the first tube, out of the second face of the first tube, through the tube joint, into the first face of the second tube, through the second tube, and then out of the second face of the second tube. Generally, the second face of the first pyrolysis-furnace tube has substantially the same exterior cross-section as the second pyrolysis-furnace tube.

The tube joint is generally made by counterboring the second face of the first tube and the first face of the second tube. For example, the second face of the first pyrolysis tube can have first and second counterbores. The first counterbore extends away from the second face to a first location a distance L/2 into the first furnace tube, the first counterbore being a substantially cylindrical counterbore with L being in the range of from $(t_2/t_1) \cdot 2.5$ cm to $(t_2/t_1) \cdot 12.7$ cm. The second counterbore is a substantially conical counterbore beginning at the first location and extending outward at a conical angle in the range of from 5.0° to 20.0°.

Likewise, the first face of the second pyrolysis tube has (a) a first counterbore, the first counterbore being a substantially cylindrical counterbore extending away from the first face to a second location a distance L'/2 into the second furnace tube, with L' being in the range of from $(t_2/t_1') \cdot 2.5$ cm to $(t_2/t_1') \cdot 12.7$ cm, and (b) a second counterbore, the second counterbore being a substantially conical counterbore beginning at the second location with the conical angle being in the range of from 5.0° to 20.0°.

Optionally, a J-bevel of V-bevel is used for joining the outer surface of the first tube at the first tube's second face to the outer surface of the second tube at the second tube's first face. For example, the second face of the first pyrolysis tube can further comprise a j-bevel weld prep having a lip, the weld prep being cut into the outer surface to provide (a) a lip thickness in the range of from $t_1/8$ to $t_1/4$, (b) a lip length in the range of from $t_1/2$ to $t_1/4$, and (c) a bevel angle in the range of from 15° to 25°, wherein the bevel angle intersects the outer surface at a third location. Likewise the first face of the second pyrolysis tube can further comprise a j-bevel weld prep having a lip, the weld prep being cut into the outer surface to provide (a) a lip thickness in the range of from $t_1'/8$ to $t_1'/4$, (b) a lip length in the range of from $t_1'/2$ to $t_1'/4$, and (c) a bevel angle in the range of from 15° to 25°, wherein the bevel angle intersects the outer surface at the fourth location. Optionally, the first location and the third location are separated by a longitudinal distance $\geq t_1/4$; and the second location and the fourth location are separated by a longitudinal distance $\geq t_1'/4$. The tube joint can be a weld, e.g., the inner surfaces of the first and second tubes can be joined by welding at the inner weld prep at the tube joint and the outer surfaces of the first and second tubes can be joined by welding a the outer weld prep. Optionally, the first location and the third location are separated by a longitudinal distance $\geq t_1/2$; and the second location and the fourth location are separated by a longitudinal distance $\geq t_1'/2$.

In certain aspects, the first pyrolysis furnace tube comprises 22 wt. % to 28 wt. % chromium, and 32 wt. % to 38 wt. % nickel, based on the weight of the first pyrolysis furnace tube and the second pyrolysis furnace tube comprises 42 wt. % to 48 wt. % chromium, and 32 wt. % to 38 wt. % nickel, based on the weight of the second pyrolysis furnace tube.

The shape of the outer surfaces of the tubes is not critical. In certain aspects, the outer surfaces of the first and second tubes are each cylindrical surfaces, each outer cylindrical surface having a substantially uniform outer diameter in the range of from about 1.5 inches (3.8 cm) to 12 inches (30 cm), the inner surface of the first and second tubes is a finned cylindrical surface, and the inner surface is substantially concentric with the outer surface.

Optionally, the joined pyrolysis furnace tubes have one or more of the following properties:

(i) L is in the range of from $(t_2/t_1) \cdot 2.5$ cm to $(t_2/t_1)$, L' is in the range of from $(t_2/t_1) \cdot 2.5$ cm to $(t_2/t_1) \cdot 5.1$ cm, $t_2 \leq t_1$, and $t_2' \leq t_i'$.

(ii) The fins of the first and second tubes are elongated helixes.

(iii) The fins of the first and second tubes are evenly-spaced around the circumference of the inside surface and have sectional shapes of waves.

(iv) N and N' are each independently in the range of from 6 to 36.

(v) The values of $t_1$ and $t_1'$ are in the range of from 0.25 inches (0.64 cm) to 0.75 inches (1.91 cm), $t_2$ and $t_2'$ are in the range of from 0.125 inches (0.32) to 0.375 inches (0.95 cm), $t_2 \leq t_1/2$ and $t_2' \leq t_1'/2$.

(vi) L is substantially equal to L', $t_1$ is substantially equal to $t_1'$, $t_2$ is substantially equal to $t_2'$, and N is substantially equal to N'.

(vii) The first and second pyrolysis-furnace tubes each independently have a total length in the range of from about 2 feet (60 cm) to about 20 feet (600 cm).

II. A Hydrocarbon Conversion Process Utilizing Joined Pyrolysis Furnace Tubes

In certain aspects, the invention relates to a hydrocarbon conversion process. The process can begin by providing a first mixture comprising water and hydrocarbon, the hydrocarbon comprising ≥75.0 wt. % of alkane having two or three carbon atoms and mixtures thereof. The process can be carried out in one or more pyrolysis furnaces, e.g., a pyrolysis furnace comprising a radiant section which includes one or more radiant coils, with each of the radiant coils comprising at least one joined pyrolysis-furnace tube. The joined pyrolysis-furnace tubes can be selected from those described in the preceding Aspect I.

Optionally, the first mixture's hydrocarbon comprises ≥75.0 wt. % ethane based on the weight of the first mixture's hydrocarbons. If desired, the first mixture can further comprise diluent, e.g., 0.20 to 1.0 weight of steam per weight of hydrocarbon.

Optionally, the pyrolysis conditions include one or more of:

(i) a maximum hydrocarbon temperature in the range of 700° C. to 1100° C.;

(ii) a pressure in the range of from 1.0 to 5.0 bar (absolute); and (iii) a residence time in the radiant coil in the range of from 0.10 to 2.0 seconds.

Example 1

This is a tube joint design for a retrofit of new radiant coils in an existing pyrolysis furnace designed for steam cracking primarily ethane or E/P mix which requires subjecting the furnace tubes to a considerably higher temperature during cracking than does steam cracking propane or liquid feeds such as naphtha. In this example, a serpentine radiant section coil is utilized which requires joining tubes with intermediate welds.

Due to the high temperatures encountered during ethane cracking, the tubes utilize a steel alloy containing 35% chromium and 45% nickel plus micro alloying elements.

The tubes have internal fins for increasing heat transfer performance. The tubes are joined in pairs, with the first tube being joined to the second by a butt-weld with a J-type weld prep. In this example, both tubes have 30 internal fins. The tubes to be joined have substantially the same interior and exterior dimensions, and substantially the same weld-prep configuration.

Referring to FIG. 2, both of the tubes have an outside diameter 50 of 6 inch (15 cm) and an inside diameter 62 of 5.25 inch (13.3 cm), the fin height $t_2$ is 0.18 inch (0.46 cm) and the minimum tube metal thickness $t_1$ is 0.375 inch (0.95 cm). Referring to FIGS. 2 and 3, the tube is provided with a cylindrical counterbore to a depth 80 of 0.50 inch (1.3 cm), followed by a conical counterbore at a 15° angle φ 84 which progresses inward until the fin reaches its full height. The outside of the tube is turned down to provide a lip having a thickness 76 of 0.0625 inch (0.16 cm), the lip extending parallel to the counterbore for a length 78 of 0.125 inch (0.32 cm), and then outward at an angle 72 of 20° for the weld prep bevel angle θ. The distance L/2 is then 0.50 inch (1.3 cm) and L is 1.00 inch (2.54 cm). Applying formula (I), the offset C is 0.261 inch (0.66 cm). Since $t_1$ is 0.375 inch (0.95 cm), the offset C=$t_1$/1.44.

Example 2

This is another tube joint design to retrofit new radiant coils in an existing pyrolysis furnace designed for steam cracking primarily ethane or E/P mix, in a serpentine radiant section coil.

In Example 2, the tubes are exposed to a temperature that is about 0.75 to 0.90 times that of Example 1, so that the tubes utilize a steel alloy containing 25% chromium and 35% nickel plus micro alloying elements.

The tubes will be installed in pairs, with the first tube being joined to the second by a butt-weld with a J-type weld prep. In this example, both tubes have 24 internal fins and the same dimensions.

Referring to FIG. 2, both of the tubes have an outside diameter 50 of 6 inch (15 cm) and an inside diameter 62 of 4.25 inch (10.8 cm), the fin height $t_2$ is 0.18 inch (0.46 cm) and the minimum tube metal thickness $t_r$ is 0.325 inch (0.83 cm). Referring to FIGS. 2 and 3, the tube is provided with a cylindrical counterbore to a depth 80 of 0.50 inch (1.3 cm), followed by a conical counterbore at a 15° angle φ 84 which progresses inward until the fin reaches its full height. The outside of the tube is turned down to provide a lip having a thickness 76 of 0.0625 (0.16 cm) inch, the lip extending parallel to the counterbore for a length 78 of 0.125 inch (0.32 cm), and then outward at an angle 72 of 20° for the weld prep bevel angle θ. The distance L/2 is then 0.50 inch (1.3 cm) and L is 1.00 inch (2.54 cm). Applying formula (I), the offset C is 0.279 inch (0.71 cm). Since $t_1$ is 0.325 inch (0.83 cm), the offset $C = t_1/1.16$.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the example and descriptions set forth herein, but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

The invention claimed is:

1. A hydrocarbon conversion process, comprising:
    (1) providing a first mixture comprising water and hydrocarbon, the hydrocarbon comprising ≥75.0 wt. % of alkane having two or three carbon atoms and mixtures thereof;
    (2) providing a pyrolysis furnace, the pyrolysis furnace comprising a radiant section comprising one or more radiant coils comprising at least one joined pyrolysis-furnace tube which comprises a first and a second pyrolysis-furnace tube, wherein
        (a) the first pyrolysis-furnace tube, the first pyrolysis furnace tube having (i) an outer surface, (ii) an inner surface, (iii) first and second faces, and (iv) the inner surface having N fins, each fin comprising a fin tip adjacent to two fin roots, wherein (a) the outer surface and the fin roots are separated by an average distance $t_1$, (b) each fin tip protrudes inward an average distance $t_2$ from the fin root, (c) the first pyrolysis furnace tube comprises ≥33.0 wt. % chromium and ≥43.0 wt. % nickel, based on the weight of the first pyrolysis furnace tube, and (d) N≥6;
        (b) the second pyrolysis-furnace tube, the second pyrolysis furnace tube having (i) an outer surface, (ii) an inner surface, (iii) first and second faces, and (iv) the inner surface having N' fins, each fin comprising a fin tip adjacent to two fin roots, wherein (a) the outer surface and the fin roots are separated by an average distance $t_1'$, (b) each fin tip protrudes inward an average distance $t_2'$ from the fin root, (c) the second pyrolysis furnace tube comprises ≥33.0 wt. % chromium and ≥43.0 wt. % nickel, based on the weight of the second pyrolysis furnace tube, and (d) N'≥6; and
        (c) a tube joint, the tube joint connecting the first and second pyrolysis furnace tubes and being open to the flow of the first mixture, wherein
            (i) the second face of the first pyrolysis furnace tube is joined to the first face of the second pyrolysis-furnace tube, the second face of the first pyrolysis-furnace tube having substantially the same exterior cross-section as the second pyrolysis-furnace tube,
            (ii) the second face of the first pyrolysis tube has (a) a first counterbore extending away from the first face to a first location a distance L/2 into the first furnace tube, the first counterbore being a substantially uniform counterbore with L being in the range of from $(t_2/t_1) \cdot 2.5$ cm to $(t_2/t_1) \cdot 12.7$ cm, and (b) a second counterbore, the second counterbore being a substantially conical counterbore beginning at the first location and having a conical angle in the range of from 5.0° to 20.0°, and
            (iii) the first face of the second pyrolysis tube has (a) a first counterbore, the first counterbore being a substantially uniform counterbore extending away from the second face to a second location a distance L'/2 into the second furnace tube, with L' being in the range of from $(t_2'/t_1') \cdot 2.5$ cm to $(t_2'/t_1') \cdot 12.7$ cm, and (b) a second counterbore, the second counterbore being a substantially conical counterbore beginning at the second location with the conical angle being in the range of from 5.0° to 20.0°;
    (3) conducting the first mixture through the at least one joined pyrolysis-furnace tube to expose the first mixture to a temperature ≥400° C. under pyrolysis conditions and convert at least a portion of the first mixture's alkane to $C_2$ unsaturates; wherein the first mixture further comprises 0.20 to 1.0 weight of steam per weight of hydrocarbon and the pyrolysis conditions include one or more of:
(i) a maximum hydrocarbon temperature in the range of 700° C. to 1100° C.;
(ii) a pressure in the range of from 1.0 to 5.0 bar (absolute); and
(iii) a residence time in the radiant coil in the range of from 0.10 to 2.0 seconds.

2. The process of claim 1, wherein
(i) the second face of the first pyrolysis tube further comprise a j-bevel weld prep having a lip, the weld prep being cut into the outer surface to provide (a) a lip thickness in the range of from $t_1/8$ to $t_1/4$, (b) a lip length in the range of from $t_1/2$ to $t_1/4$, and (c) a bevel angle in the range of from 15° to 25°, wherein the bevel angle intersects the outer surface at a third location;
(ii) the first face of the second pyrolysis tube further comprise a j-bevel weld prep having a lip, the weld prep being cut into the outer surface to provide (a) a lip thickness in the range of from $t_1'/8$ to $t_1'/4$, (b) a lip length in the range of from $t_1'/2$ to $t_1'/4$, and (c) a bevel angle in the range of from 15° to 25°, wherein the bevel angle intersects the outer surface at a fourth location;

(iii) the first location and the third location are separated by a longitudinal distance $\geq t_1/2$;

(iv) the second location and the fourth location are separated by a longitudinal distance $\geq t_1'/2$; and (v) the tube joint is a weld.

3. The process of claim 1, wherein the first mixture's hydrocarbon comprises $\geq 75.0$ wt. % ethane based on the weight of the first mixture's hydrocarbons.

4. The process of claim 1, wherein the outer surface of the first and second tubes is a cylindrical surface having a substantially uniform outer diameter in the range of from about 1.5 inches (3.8 cm) to 12 inches (30 cm), the inner surface of the first and second tubes is a finned cylindrical surface, and the inner surface is substantially concentric with the outer surface.

5. The process of claim 1, wherein L is in the range of from $(t_2/t_1) \cdot 1.0$ inch to $(t_2/t_1) \cdot 2.0$ inch, L' is in the range of from $(t_2'/t_1') \cdot 2.5$ cm to $(t_2'/t_1') \cdot 5.1$ cm, $t_2 \leq t_1$, and $t_2' \leq t_1'$.

6. The process of claim 1, wherein the fins are elongated helixes.

7. The process of claim 1, wherein the fins are evenly-spaced around the circumference of the inside surface and have sectional shapes of waves.

8. The process of claim 1, wherein N and N' are each in the range of from 6 to 36.

9. The process of claim 1, wherein $t_1$ and $t_1'$ are in the range of from 0.25 inch (0.64 cm) to 0.75 inches (1.9 cm), $t_2$ and $t_2'$ are in the range of from 0.125 inches (0.32 cm) to 0.375 inches (0.95 cm), $t_2 \leq t_1/2$, and $t_2' \leq t_1'/2$.

10. The process of claim 1, wherein L is substantially equal to L', $t_1$ is substantially equal to $t_1'$, $t_2$ is substantially equal to $t_2'$, and N is substantially equal to N'.

11. The process of claim 1, wherein the first and second pyrolysis-furnace tubes each independently have a total length in the range of from about 2 feet (60 cm) to about 20 feet (600 cm).

* * * * *